US008934737B1

(12) United States Patent
Solliday-McRoy

(10) Patent No.: US 8,934,737 B1
(45) Date of Patent: Jan. 13, 2015

(54) SYSTEM AND METHOD TO DE-IDENTIFY AN ACQUIRED FILE

(71) Applicant: General Electric Company, Schenectady, NY (US)

(72) Inventor: Jeffrey Dale Solliday-McRoy, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 160 days.

(21) Appl. No.: 13/648,791

(22) Filed: Oct. 10, 2012

(51) Int. Cl.
*G06K 9/60* (2006.01)

(52) U.S. Cl.
USPC ........... 382/305; 382/128; 382/131; 382/132; 382/299

(58) Field of Classification Search
USPC .......... 382/128, 131, 132, 299, 305; 709/206, 709/217, 203; 707/722, 736; 726/11
See application file for complete search history.

(56) References Cited

U.S. PATENT DOCUMENTS

| 6,411,836 | B1 | 6/2002 | Patel et al. |
| 6,501,849 | B1 | 12/2002 | Gupta et al. |
| 6,564,256 | B1 | 5/2003 | Tanaka |
| 2002/0016718 | A1 | 2/2002 | Rothschild et al. |
| 2005/0187787 | A1 | 8/2005 | Tomlinson et al. |
| 2006/0253502 | A1 | 11/2006 | Raman et al. |
| 2008/0021741 | A1 | 1/2008 | Holla et al. |
| 2008/0120132 | A1* | 5/2008 | Wegenkittl et al. ............... 705/2 |
| 2010/0122336 | A1* | 5/2010 | Hunt et al. ..................... 726/11 |
| 2011/0002523 | A1* | 1/2011 | Prakash et al. ................ 382/131 |
| 2011/0161450 | A1* | 6/2011 | Westin et al. ................. 709/206 |

OTHER PUBLICATIONS

DICOM Standards Committee, Working Group 18 Clinical Trials, "Digital Imaging and Communications in Medicine (DICOM): Supplement 142: Clinical Trial De-Identification Profiles", (Jan. 25, 2011), <>, pp. 3-8 and 29-34.

* cited by examiner

Primary Examiner — Ali Bayat

(57) ABSTRACT

A system and method to process an image file from an image source before storage on a physical storage medium. The image file can include an image data and an identifier data of a person. The system can comprise a receiver connected in communication to receive the image file from the image source. The receiver can be configured to de-identify the identifier data from each part of the image file as presented to the receiver prior to being subsequently stored on the physical storage medium.

10 Claims, 3 Drawing Sheets

SYSTEM AND METHOD TO DE-IDENTIFY AN ACQUIRED FILE

TECHNICAL FIELD

The subject herein generally relates to a system and method to de-identify an acquired file, and more specifically, to de-identify an acquired image file prior to subsequent storage.

BACKGROUND

Information may often be acquired in the course of business having private, identifier data that can bias or directly associated information to a person. For example, hospitals and other medical facilities (e.g., imaging centers, cardiology treatment centers, emergency rooms, surgical suites, etc.) include many medical equipment systems, some operable to create an image file having image data combined or integrated with identifier data of a person associated with the acquired image data. Such image files are then utilized by the hospital or medical setting to deliver healthcare to the person. In many instances, there is a need for a secondary re-use of the image data in the image file, such as in clinical trials, teaching instruction, or for publication. In addition to privacy concerns, there can also be proprietary concerns with secondary re-use of information involving communication to an external medium for viewing or storage.

A problem with the secondary re-use of certain information files include privacy concerns for the identifier data included in the information files being viewed or stored on an outside media. There is a need to automatically de-identify information having privacy or proprietary concerns prior to external viewing or external storage of the information.

The above-mentioned problem can be addressed by the subject matter described herein in the following description.

BRIEF SUMMARY

The system and method of the subject matter described herein can be directed to provide a system or method to de-identify identifier data stored with image data on an image before viewing or storage outside of the image source 110, such as for example in a clinical setting or hospital.

According to one embodiment, a system to process an image file from an image source before storage on a physical storage medium is provided. The image file can include an image data and an identifier data of a person. The system can comprise a receiver connected in communication to receive the image file from the image source. The receiver can be configured to de-identify the identifier data from each part of the image file as presented to the receiver prior to being subsequently stored on the physical storage medium.

According to another embodiment, a method to process an image file communicated from an image source before storage on a physical storage medium is provided. The image file can include an image data and an identifier data of a person. The method can comprise the steps of: receiving the image file at a receiver connected in communication with the image source; and de-identifying the identifier data from each part of the image file as presented to the receiver prior to being subsequently stored on a physical storage medium.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
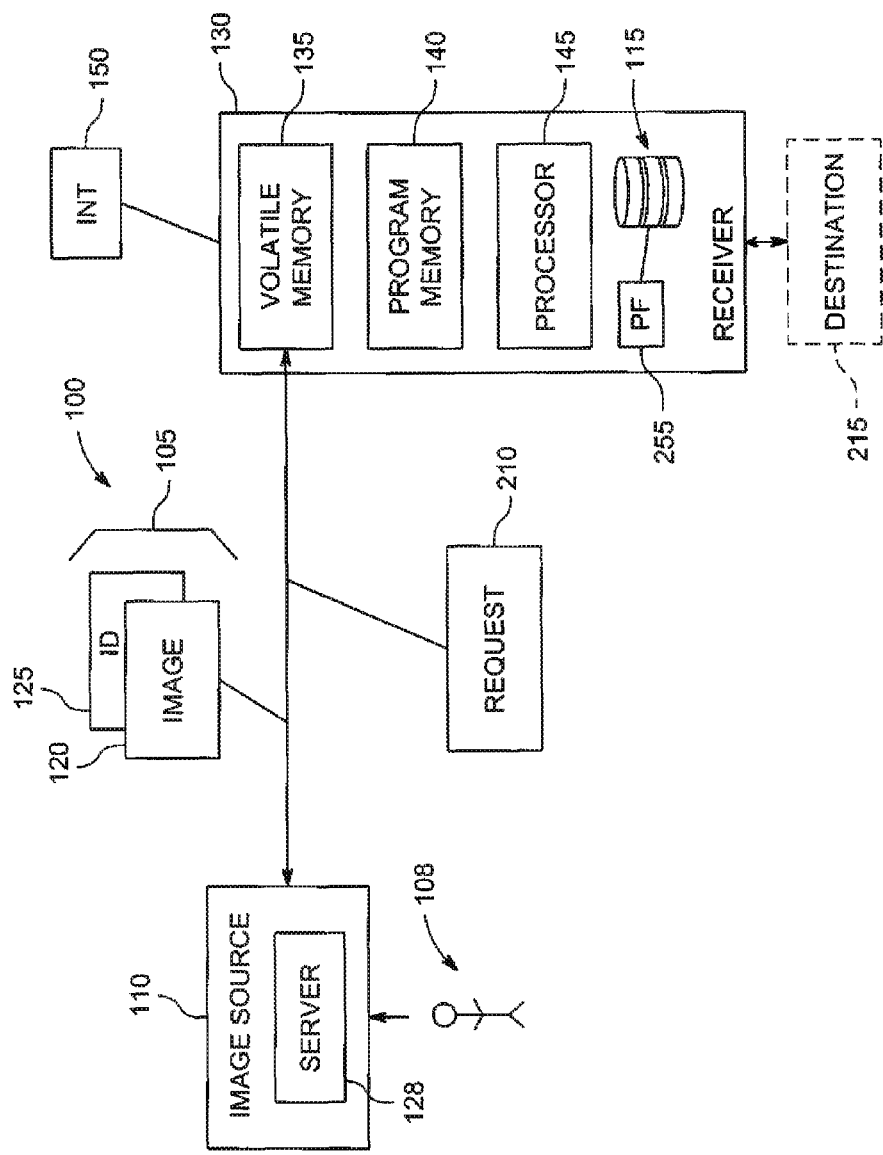
FIG. 1 is a schematic diagram of an embodiment of a system to process an image file from an image source before storage on a physical storage medium in accordance with the subject matter described herein.

FIG. 1 illustrates a schematic diagram of an embodiment of a system 100 to process an image file 105 of a person 108 acquired from an image source 110 before storage of the image file 105 on a physical or tangible storage medium 115. More specifically, the system 100 is configured to de-identify the image file 105.

An embodiment of the image file 105 includes an image data 120 and an identifier data 125 of the person 108. The image file 105 can be acquired during the course of delivery of healthcare where the person 108 is a patient. In such an example, the identifier data 125 can generally include individually identifiable information, where de-identification is desired to protect the person's privacy. The identifier data 125 can be included in the image file 105 as, for example, metadata, header data, private information, attributes, etc. Examples of identifier data 125 can include identity and demographic characteristics of the person, identity of any responsible parties or family members; identify of any personnel (e.g., clinician, doctor, technician, etc.) involved in acquiring the image file 105, identity of the organization involved in acquiring the image file or delivery of healthcare to the person, information (e.g., unique identifications assigned by organization, dates, times, etc.) that can be used to match instances if given access to the image file, or private attributes (e.g., trade secret or confidential information that can be proprietary to a device manufacturer or vendor). The identifier data 125 is not limited to information that directly relates the person's identity to the image file 105, but can include that information that might assist or create a bias in recovering the identity of the person associated with the image file 105. The image data 120 in the image file 105 can be in a DICOM format, ACR/NEMA, DEFF, Qsh, Interfile, Papyrus, etc.

The image file 120 can acquired from multiple types of image sources 110, such as a picture archival system (PACS), a CT image scanner, an MR image scanner, an Ultrasound image scanner, enterprise image archive, etc. and is not limiting on the subject matter described herein. The image source 110 can include a server 128 connected in communication and configured to transmit the requested image file 105 to the system 100.

De-identifying can include removing identifier data, encrypting, aggregating, or replacing the identifier data with a different value (e.g., dummy value) that does not allow or sufficiently inhibits recovering the individually identity of the person. The system 100 can be configured to de-identify the image file 105 and likewise preserve or retain certain attributes or information (e.g., image or pixel data) in the image file 105 desired for subsequent analysis, secondary re-use, etc. or other known applications described herein or known in the art.

Applications of the system 100 where de-identifying can be desired include creating teaching files, generating publications, release of image files for secondary re-use (e.g., research, service analysis), etc. where privacy concerns exist.

An embodiment of the system 100 can include a receiver 130 having the physical storage medium 115 in communication with a volatile memory 135, and a program memory 140 having a series of modules of computer programming instructions for execution by a processor 145. The volatile memory 135 can configured to receive each of the parts of the image file 105 as presented to the receiver and prior to being written or stored on the physical storage medium. An embodiment of the physical or tangible storage medium 115 can be a non-transitory, computer-readable medium such as a hard-drive of a stand-alone computer, CD, DVD, etc. The receiver 130 can be a stand-alone computer or server, but is not limiting on the subject matter described herein.

The program memory 140 can include a plurality of modules of program instructions for execution by the processor 145 in performing steps to process each of the plurality of parts of the image file 105 in removing the identifier data 125 while the parts of the image file 105 are in the volatile memory 135 and not yet written to the physical storage medium 115. The modules of program instructions will be described in more detail in the description below.

The system 100 can further include an interface 150 having an input and output connected in communication with the receiver 130 so as to generate a request 210 for the image file 105 from the image source 110. Examples of input of the interface 150 can include a keyboard, mouse, touchscreen, toggles, etc. and is not limiting on the subject matter described herein. Examples the output of the interface 150 can include a monitor, speaker, touchscreen, etc. and is not limiting on the subject matter described herein. The request 155 can be originated via the interface 150 or can be automatically generated at time of creation of the image file 105 or on a periodic batch dump basis via program instructions stored in the program memory 140 for execution by the processor 145.

Having provided an embodiment of one construction of the system 100 in accordance with above-description, the following is a description of an embodiment of a method 200 (See FIG. 2) to operate the system 100 in accordance with the subject matter described herein. It should also be understood that the sequence of the acts or steps of the method 200 as discussed in the foregoing description can vary. Also, it should be understood that the method 200 may not require each act or step in the foregoing description, or may include additional acts or steps not disclosed herein. It should also be understood that one or more of the steps of the method 200 can be represented by one or more modules of computer-readable program instructions stored in the program memory 140 for execution by the processor 145.

Figure 2:
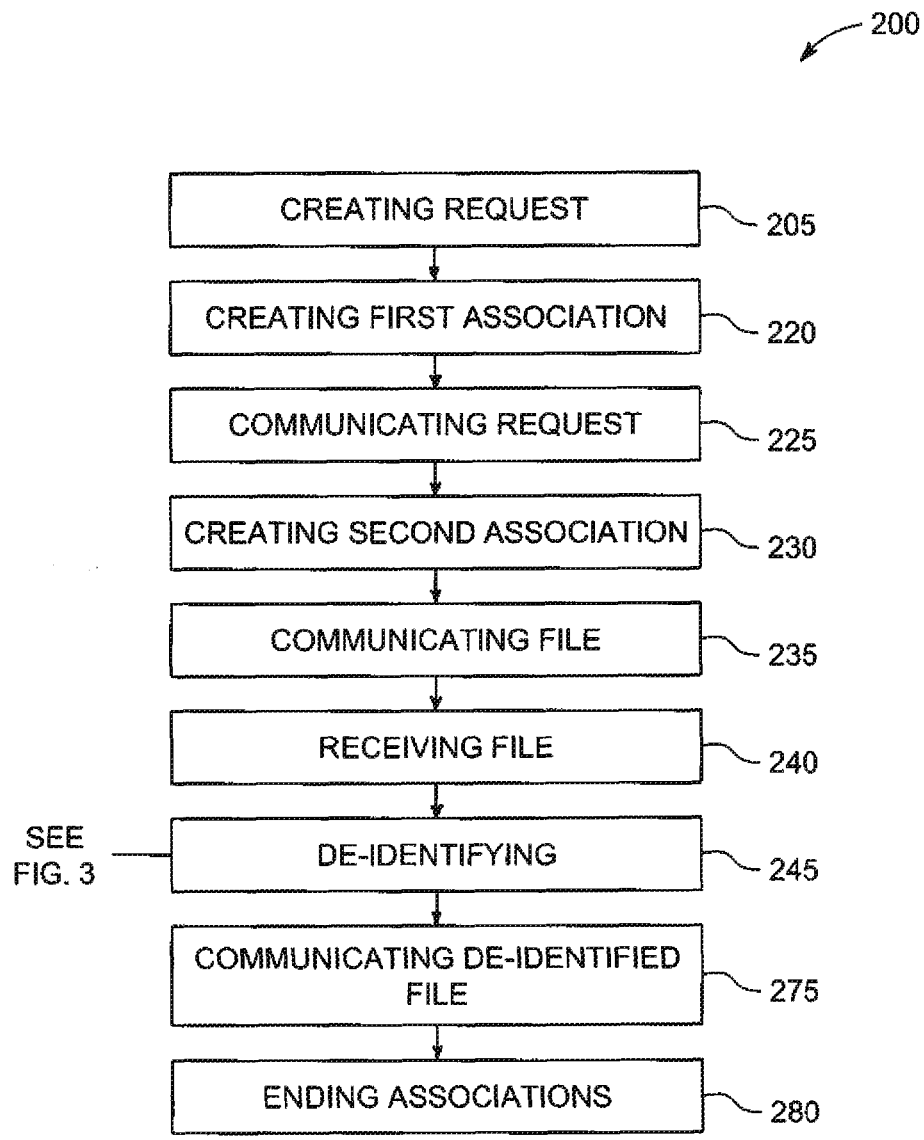
FIG. 2 is a schematic flow diagram of an embodiment of a method of operating the system of FIG. 1 in accordance with subject matter described herein.

Assume for sake of example that the image source 110 is a picture archival system (PACS) that includes the image file 105 in DICOM format acquired by a CT image scanner. Also assume that the image file 105 can include the image data 120 and the identifier data 125 associated with the image data 120. As shown in FIG. 2 in referring to the system 100 of FIG. 1, step 205 can include the server 128 associated with the image source 110 creating a request or query 210 from the system 100 for the image data 120 in the image file 105 after de-identifying the identifier data 125.

Assume that the request 210 includes a destination 215 to move the image file 105 after de-identifying of the identifier data 125 by the system 100. One embodiment of the destination 215 can be the physical storage medium 115 of the receiver 130. Other examples of the destination 215 can be a remote entity (shown in dashed line, such as a client server, remote database, etc.

In response, step 220 can include the receiver 130 generating or opening a first association to create a communication path to the server 128 associated with the image source 110. Step 225 can include communicating the request 210 or query from the receiver 130 to the server 128. Step 230 can include the receiver 130 opening a second association to create a communication path with the server 128 associated with the image source 110. Step 235 can include communicating the image file 105 from the image source 110 via the server 128 to the receiver 130. Step 240 can include receiving the image file 105 at the receiver 130 from the image source 110.

Step 245 can include de-identifying the identifier data from each part of the image file as presented to the receiver 130 and prior to being subsequently stored on the physical storage medium 115. The receiver 130 can include the volatile memory 135 holding each part of the image file 105 for de-identifying of the identifier data 125 by the receiver 130 prior to storing the remaining image data 120 of the image file 105 on the physical storage medium 115.

Figure 3:
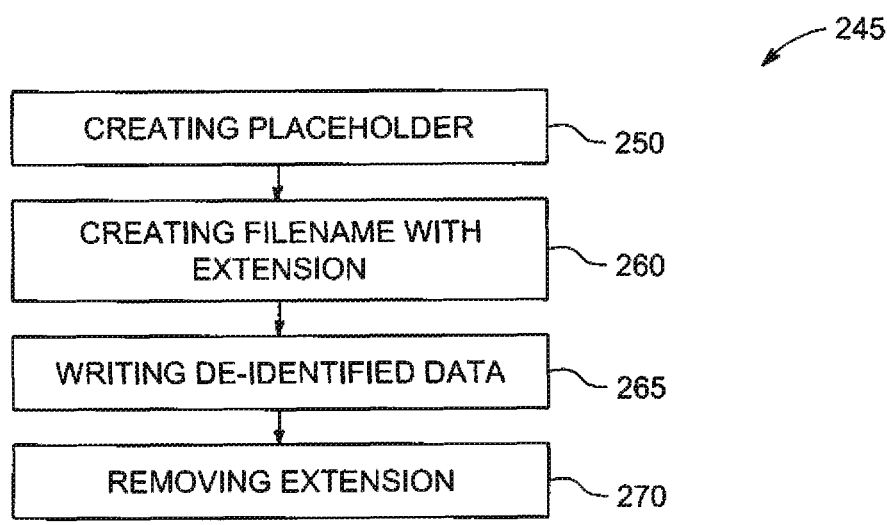
FIG. 3 is a schematic flow diagram of an embodiment of a method of de-identifying with the system of FIG. 1 in accordance with subject matter described herein.

The receiver 130 can include program instructions stored in the program memory 140 for execution by the processor 145 in identifying the identifier data 125 in each part of the image file 105 for de-identifying from the remainder of the image file 105. Under the de-identifying step 245 and referring to FIG. 3, the processor 145 can execute program instructions in the program memory 140 to perform: the step 250 of generating a placeholder file 255 on the physical storage medium 115 in response to receiving the image file 105 from the image source 110; step 260 of creating a filename having a temporary extension (e.g., ".tmp" or ".part") for the placeholder file 255 to receive the remaining image data 120 after de-identifying of the identifier data 125 in each part of the image file 105 while in the volatile memory 135, step 265 of writing each part of the remaining image data 120 in the image file 105 to the placeholder file 255 after de-identifying of the identifier data 125 in the volatile memory 135, and step 270 of removing of the extension from the filename of the placeholder file 240 after writing all of the de-identified parts of the image file 105 to the placeholder file 240. The placeholder file 240 can be empty prior to receiving the image file 105.

Step 275 can include communicating the de-identified image file (ie., the placeholder file 235) to the destination 215 per the request or query 210. Step 280 can include the receiver 130 and the image source 110 ending the associations to create the communication pathways therebetween.

A technical effect of the above-described access system 100 and method 200 can include providing an automatic, integrated solution to de-identify image files 105 directly with responding to a need for information having privacy concerns, thereby reducing a risk of private/protected identifier data 125 being viewed or at rest on an external physical storage medium 115. The system 100 and method 200 can provide a solution for compliance in clinical settings where de-identifying of image files 105 can be a requirement before viewing or storage outside of the clinical setting. The system 100 and method 200 can provide the ability to automatically de-identify information having privacy or proprietary concerns prior to external viewing or storage of the information at the external storage medium of the designation 215. Although this system 100 and method 200 can be described with respect to the healthcare field, it should be understood that the system 100 and method 200 can also be applied to the asset management, research, and service fields and is not limiting on the subject matter described herein.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system to process an image file from an image source before storage on a physical storage medium, the image file including an image data and an identifier data of a person, the system comprising:
   a receiver connected in communication to receive the image file from the image source, the receiver configured to de-identify the identifier data from each part of the image file as presented to the receiver prior to being subsequently stored on the physical storage medium, wherein to de-identify the identifier data, the receiver generates a placeholder file on the physical storage medium in response to receiving the image file from the image source, wherein the placeholder file is empty prior to receiving the image file from the receiver, wherein the placeholder file includes a filename having an extension prior to receiving the image file from the receiver, wherein the extension is removed from the filename after the identifier data is removed from the image file in the volatile memory, and wherein the receiver writes the image file to the placeholder file on the physical storage medium after the identifier data is removed.

2. The system of claim 1, wherein the receiver includes a volatile memory operable to hold each part of the image file to de-identify prior to the image file being stored on the physical storage medium.

3. The system of claim 2, wherein the receiver includes a plurality of program instructions for execution by processor in performing the step of:
   identifying the identifier data in each part of the image file.

4. The system of claim 1, wherein the receiver is configured to de-identify the identifier data by performing at least one of removing the identifier data and replacing the identifier data.

5. The system of claim 1, wherein the receiver receives the image file in response to a query communicated via the receiver.

6. A method to process an image file communicated from an image source before storage on a physical storage medium, the image file including an image data and an identifier data of a person, the method comprising the steps of:
   receiving the image file at a receiver connected in communication with the image source; and
   de-identifying the identifier data from each part of the image file as presented to the receiver prior to being subsequently stored on a physical storage medium, wherein the step of de-identifying includes, generating a placeholder file on the physical storage medium in response to receiving the image file from the image source, creating a filename having an extension for the placeholder file prior to the step of receiving image file, removing the extension from the filename after the identifier data is removed from the image file, and writing the image file to the placeholder file after the identifier data is one of removed and replaced.

7. The method of claim 6, wherein the receiver includes a volatile memory, and further comprising the step of holding each part of the image file for de-identifying prior to storing image file on the physical storage medium.

8. The method of claim 7, further comprising the step of identifying the identifier data in each part of the image file.

9. The method of claim 6, wherein the step of de-identifying the identifier data includes at least one of removing the identifier data and replacing the identifier data.

10. The method of claim 6, wherein the step of receiving the image file is in response to communicating a query via the receiver to the image source.

* * * * *